US009829586B2

(12) United States Patent
Göderer et al.

(10) Patent No.: US 9,829,586 B2
(45) Date of Patent: Nov. 28, 2017

(54) DETECTION OF X-RAYS, AND X-RAY DETECTOR SYSTEM

(71) Applicant: Siemens Aktiengesellschaft, Munich (DE)

(72) Inventors: Edgar Göderer, Forchheim (DE); Peter Hackenschmied, Nuremberg (DE); Steffen Kappler, Effeltrich (DE); Björn Kreisler, Hausen (DE); Miguel Labayen De Inza, Forchheim (DE); Daniel Niederlöhner, Erlangen (DE); Mario Reinwand, Breitbrunn (DE); Christian Schröter, Bamberg (DE); Matthias Strassburg, Klangenfurt (AT); Stefan Wirth, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 198 days.

(21) Appl. No.: 14/418,378

(22) PCT Filed: Jul. 9, 2013

(86) PCT No.: PCT/EP2013/064495
§ 371 (c)(1),
(2) Date: Jan. 29, 2015

(87) PCT Pub. No.: WO2014/019818
PCT Pub. Date: Feb. 6, 2014

(65) Prior Publication Data
US 2015/0212215 A1 Jul. 30, 2015

(30) Foreign Application Priority Data

Jul. 31, 2012 (DE) .................. 10 2012 213 494

(51) Int. Cl.
*G01T 1/24* (2006.01)
*G01N 23/04* (2006.01)
*G01T 1/02* (2006.01)

(52) U.S. Cl.
CPC ............ *G01T 1/244* (2013.01); *G01N 23/04* (2013.01); *G01N 23/046* (2013.01); *G01T 1/026* (2013.01); *G01T 1/24* (2013.01)

(58) Field of Classification Search
CPC combination set(s) only.
See application file for complete search history.

(56) References Cited

U.S. PATENT DOCUMENTS 5,905,772 A * 5/1999 Rutten ................. G01T 1/24
348/E3.052
7,426,259 B2 * 9/2008 Weisfield ............. H04N 5/32
250/370.09

(Continued)

FOREIGN PATENT DOCUMENTS

CN   1912651 A    2/2007
CN   101080653 A  11/2007

(Continued)

OTHER PUBLICATIONS

International Search Report PCT/ISA/210 for International Application No. PCT/EP2013/064495 dated Dec. 4, 2013.

(Continued)

*Primary Examiner* — Phillip A Johnston
*Assistant Examiner* — Hsien Tsai
(74) *Attorney, Agent, or Firm* — Harness, Dickey & Pierce, P.L.C.

(57) ABSTRACT

A method is disclosed for detecting x-rays using an x-ray detector which includes a direct-conversion semiconductor detector element. Additional radiation is supplied to the semiconductor detector element using a radiation source, (Continued)

and the supply of the additional radiation is controlled and/or regulated on the basis of a specified target value. In at least one embodiment, the target value can be specified in a variable manner over time as a sequence of target values. An x-ray detector system is further disclosed, with which the method can be carried out.

29 Claims, 6 Drawing Sheets

(56) References Cited

U.S. PATENT DOCUMENTS

| | | |
|---|---|---|
| 2007/0034807 A1 | 2/2007 | Danzer et al. |
| 2009/0238330 A1 | 9/2009 | Luhta et al. |
| 2009/0257556 A1* | 10/2009 | Okamura ............... A61B 6/585 378/62 |
| 2011/0253886 A1 | 10/2011 | Hackenschmied et al. |

FOREIGN PATENT DOCUMENTS

| | | |
|---|---|---|
| CN | 102253403 A | 11/2011 |
| EP | 1394567 A2 | 3/2004 |
| JP | H10186045 A | 7/1998 |
| JP | 2008523872 A | 7/2008 |
| JP | 2009011526 A | 1/2009 |
| KR | 101042046 B1 | 6/2011 |
| WO | WO 2006064403 A2 | 6/2006 |

OTHER PUBLICATIONS

Written Opinion of the International Searching Authority PCT/ISA/237 for International Application No. PCT/EP2013/064495 dated Dec. 4, 2013.
Chinese Office Action and English translation thereof dated Jun. 15, 2016.
Korean Office Action and English translation thereof dated Jul. 19, 2016.
Office Action for European Patent Application No. 13739178.5 issued on Mar. 7, 2017.

* cited by examiner

DETECTION OF X-RAYS, AND X-RAY DETECTOR SYSTEM

PRIORITY STATEMENT

This application is the national phase under 35 U.S.C. §371 of PCT International Application No. PCT/EP2013/064495 which has an International filing date of Jul. 9, 2013, which designated the United States of America, and which claims priority to German patent application DE 102012213494.8 filed Jul. 31, 2012, the entire contents of each of which are hereby incorporated herein by reference.

FIELD

At least one embodiment of the invention generally relates to a method for detecting x-ray radiation, an x-ray detector, an x-ray detector system, and/or a computed tomography system having a direct-conversion semiconductor detector element for detecting x-ray radiation.

BACKGROUND

Different detector systems are known for detecting x-ray radiation. Scintillation detectors are widely used in order for example to enable flux densities of x-ray radiation occurring in the field of computed tomography to be measured. Scintillation detectors initially convert x-ray radiation photochemically into light quanta which have an energy suitable for enabling for example the light quanta to be detected with the aid of a semiconductor diode (photodiode).

For the purpose of computed tomography applications, efforts are furthermore directed toward the use of what are termed direct-conversion semiconductor detector elements, which absorb x-ray radiation in the semiconductor material without prior energy conversion. In the process, so-called electron-hole pairs are generated in the semiconductor detector element. It should be emphasized that the term "direct-conversion", within the scope of the present invention, does not restrict the type of absorption of x-ray quanta in the semiconductor material. Although the description suggests a different inference, "direct-conversion semiconductor detector elements" enable both direct and indirect absorption of x-ray quanta (photon-assisted absorption). What matters with regard to the term "direct-conversion semiconductor material" is that an x-ray quantum is absorbed in the semiconductor material, in other words, in contrast to a scintillation detector, the roundabout route by way of a prior photochemical conversion of the x-ray radiation is avoided.

A certain quantity of free charge carriers are generated in the semiconductor detector element as a function of the energy of the absorbed x-ray radiation. In the process, a normally bound electron of the valence band of the semiconductor, upon absorption of x-ray radiation, gains at least so much energy that it is able, as mentioned, directly or indirectly to overcome the band gap of the semiconductor material used and in the conduction band of the semiconductor can contribute in an effectively "freely mobile" manner (the corresponding transport mechanisms in the semiconductor are known to the person skilled in the art) toward the conduction of a current. In the valence band there remains behind a vacant electron position, also referred to as a hole, which is likewise "mobile" in the valence band, which means that the generated electron vacancy can also contribute toward the conduction of a current. However, the drift or diffusion velocity may differ radically between electrons and holes.

If the freely moving charge carriers are brought into the area of influence of an electric field—for example by way of field electrodes that are connected to the semiconductor detector element, and by applying a voltage—then a photocurrent results owing to the availability of the free-moving charge carriers. By evaluating the pulse shape of the charge carrier packets (in particular the pulse height) it is possible to determine the number and the energy of the absorbed x-ray quanta or, as the case may be, of the absorbed x-ray radiation.

The drift and diffusion critical to the charge transport of the mobile charge carriers in the semiconductor, and hence to the pulse shape, are described by way of the movability (mobility p) of the free charge carriers. In particular the drift is also dependent in this case on the already mentioned electric field.

In particular it is aimed to use directly converting semiconductor detector elements based on CdTE, CdZnTe, CDZnTeSe, CdMnTe, InP, $TlBr_2$, Hgl2. However, a disadvantage with these detector materials is that the electric field in the semiconductor material, and consequently the pulse shape of the photocurrent, can vary therein in an undesirable manner. In timescales relevant to the detection of x-ray radiation, these materials have unwanted numbers of stationary defects, called "traps". These traps can intercept free-moving electrons of the conduction band or holes of the valence band and bind them in a stationary manner to the defects for a certain time. Furthermore, in the occupied or unoccupied state, the defects represent space charges. This formation of space charges is referred to as the polarization effect, as polarization for short, of the semiconductor detector element.

A disadvantageous aspect of the described effects is that the formation of space charge zones due to the traps or also the charge carrier trapping varies with respect to time as a function of the number of unoccupied or occupied traps. The electric field in the semiconductor material and the resulting pulse shape of the photocurrent may therefore be dependent on the temporal distance between absorption events, with the result that under certain conditions identical absorption events are not evaluated in a reproducible manner and a phenomenon called count rate drift occurs. In other words, the count rate of x-ray quanta for a temporally constant radiation density varies with time. Consequently, under certain conditions no unequivocal back-calculation to energy or number of absorbed x-ray quanta is possible, which means that a considerable amount of time and effort is required in order to make these detectors suitable for reliable use in imaging applications, such as in computed tomography for example.

In order to mitigate the cited polarization effects, and in particular to attenuate the time-dependent variation in the polarization during the detection of x-ray radiation, the semiconductor detector element can be irradiated.

The polarization can be varied when the defects are occupied by a corresponding charge carrier, but also when an unoccupied defect is generated. For this purpose a light source can be used, the radiation of which generates charge carriers in the semiconductor which can then be bound to the defect over a relatively long period of time. Such a defect is also referred to as a saturated defect, which, in contrast to an ionized defect, can be considered virtually charge-neutral. As a result the formation of space charge zones is varied, and in particular these can also be stabilized. The semiconductor detector element can be conditioned by this means such that an unequivocal back-calculation to the energy or count rate is possible.

In order to enable a reliable, unequivocal detection of x-ray radiation, in particular for imaging applications, it is furthermore necessary that the conditioning is likewise effected unequivocally, i.e. that the semiconductor detector element has a defined conditioning.

SUMMARY

At least one embodiment of the present invention is directed to detecting x-ray radiation in a reproducible or unequivocal manner so that the evaluation of the detected x-ray radiation satisfies for example the requirements for x-ray imaging or improves the possibilities for x-ray imaging.

At least one embodiment is directed to a method for detecting x-ray radiation, an x-ray detector system, an x-ray detector, and a computed tomography system.

According to at least one embodiment of the invention, a method for detecting x-ray radiation by way of an x-ray detector having a direct-conversion semiconductor detector element is proposed in which the additional radiation (i.e. in addition to the x-ray radiation that is to be detected) is supplied to the semiconductor detector element with the aid of a radiation source.

Accordingly, an x-ray detector system having an x-ray detector for detecting radiation of an x-ray source is proposed within the scope of at least one embodiment of the invention. The x-ray detector has a direct-conversion semiconductor detector element, i.e. the detector element at least partially absorbs the x-ray radiation of an x-ray source that is to be detected and generates a detection signal based on the absorbed x-ray radiation. The detector is suitable in particular for use in x-ray imaging, for example in a computed tomography system, a SPECT system or a PET system.

The x-ray detector system according to at least one embodiment of the invention comprises a radiation source for supplying additional radiation to the semiconductor detector element and/or a control interface for driving a radiation source. The control interface can then be used for example for driving suitable radiation sources that are already present in an x-ray system (in particular a computed tomography system) to which the detector belongs, for the purpose of supplying the conditioning radiation directly or indirectly (via another control unit that is present). The already existing x-ray source can be for example a computed tomography system.

The x-ray detector system of at least one embodiment additionally includes a control unit which controls or regulates the supply of the additional radiation on the basis of a specified nominal value. It should be emphasized in this context that in the following description the term "control unit" not only includes the possibility of controlling the supply of the compensation radiation, but may also include the possibility of regulating the supply of the compensation radiation.

Other particularly advantageous embodiments and developments of the invention will become apparent from the dependent claims as well as from the following description, wherein the independent claims of one claims category can also be developed analogously to the dependent claims of a different claims category.

BRIEF DESCRIPTION OF THE DRAWINGS

The invention is explained below once again in more detail with the aid of (usually only schematically represented) example embodiments and with reference to the attached figures. Here, like components are labeled with identical reference numerals in the different figures, in which.

DETAILED DESCRIPTION OF THE EXAMPLE EMBODIMENTS

Figure 1:
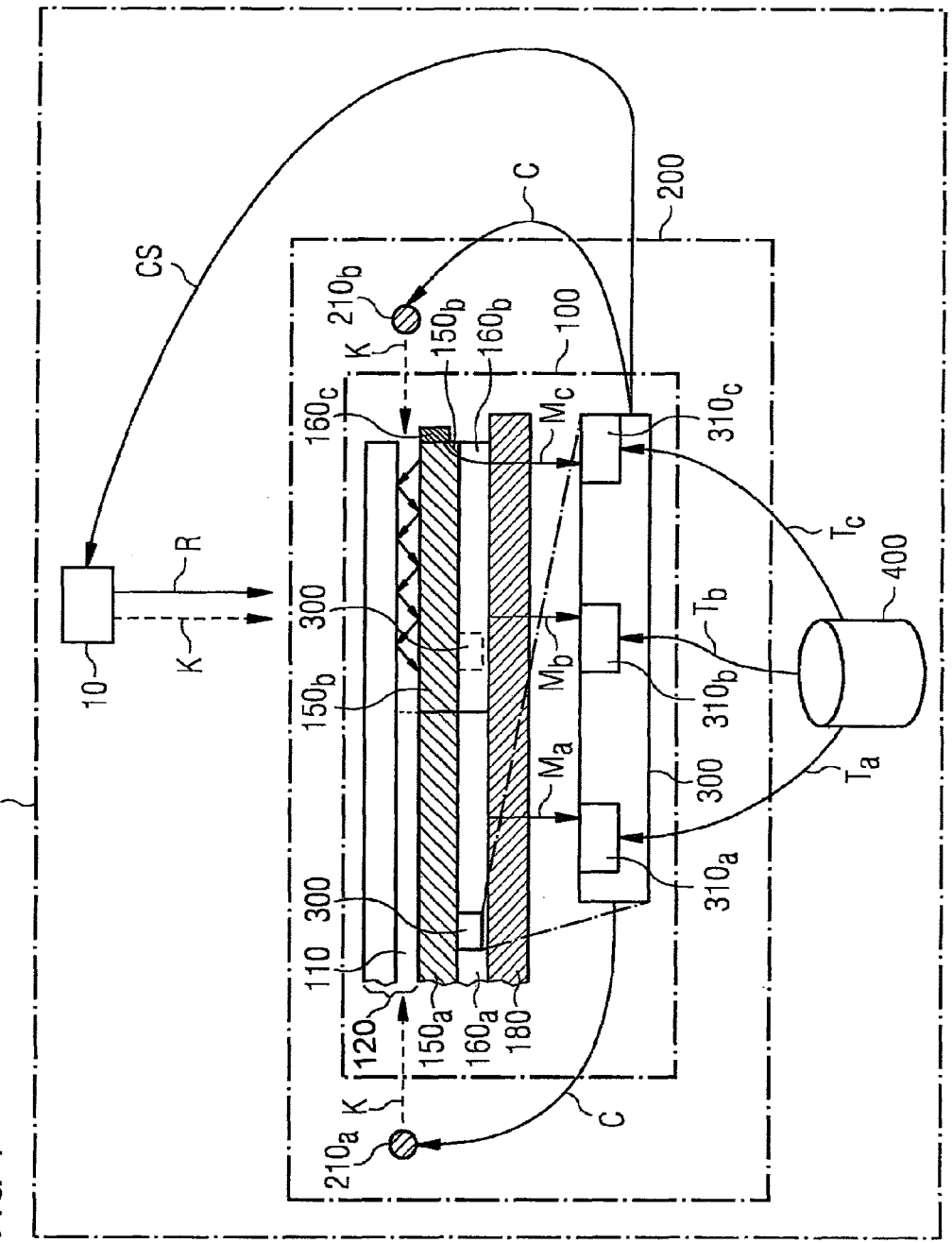
FIG. 1 shows an example embodiment of a computed tomography system having an x-ray detector system and x-ray detector which is controlled or regulated according to an example embodiment of the invention.

According to at least one embodiment of the invention, a method for detecting x-ray radiation by way of an x-ray detector having a direct-conversion semiconductor detector element is proposed in which the additional radiation (i.e. in addition to the x-ray radiation that is to be detected) is supplied to the semiconductor detector element with the aid of a radiation source.

As explained already in the introduction, the term "direct-conversion" relates to a semiconductor detector element which at least partially absorbs x-ray radiation of an x-ray source that is to be detected and generates a detection signal, i.e. in particular a detection pulse, based on the absorbed x-ray radiation. Toward that end the semiconductor detector element can comprise a plurality of field electrodes which impress an electric field into the semiconductor detector element and in that way specify one or more detection zones, each of which forms a pixel of the x-ray detector.

The additional radiation supplied, according to at least one embodiment of the invention, serves in this case for conditioning the semiconductor detector element, as already described in the introduction, and preferably for varying polarization effects in the semiconductor detector element, as likewise described in the introduction, and particularly preferably for varying the electric field (and if necessary the free path length of charge carriers) in the semiconductor detector element. In that respect the additional radiation is also referred to in the following description as "conditioning radiation".

According to at least one embodiment of the invention, the supply—or, as the case may be, indirectly the emission—of the additional radiation or conditioning radiation is controlled or regulated based on a specified nominal value.

With the aid of the nominal value, according to at least one embodiment of the invention, it can for example be specified in a reliable manner how the semiconductor detector element is conditioned or, and preferably also, how the semiconductor detector element is to be conditioned in the future for an x-ray detection measurement that is to be performed. This is based in particular on the knowledge that it is sufficient to know the conditioning, i.e. in particular the polarization or the compensation of the polarization, in order to enable an unequivocal detection of x-ray radiation.

This can also mean in particular that with the aid of the nominal value the conditioning is adapted to match the requirements of a specific x-ray detection measurement. That is to say that the nominal value is variable for different x-ray detection measurements performed at different times or also is varied during an x-ray detection measurement. For example, a specific sensitivity of the detector given by a maximum count rate may be necessary or sufficient. With the aid of the nominal value, for example a count rate, it can then be specified or established whether the semiconductor detector element is appropriately conditioned in order to attain the maximum count rate. If this is not the case, or if a lower sensitivity is sufficient, the supply of the conditioning radiation can be suitably controlled or regulated until a desired new nominal value, for example the maximum sensitivity, is reached. Starting from a state in which a current nominal value is used for the control or regulation, a desired new nominal value is also referred to in the following as a "target value".

The nominal value may be in particular a nominal measured value, in other words a value that has been measured directly or derived directly from a measurement.

This can be achieved for example with the aid of a nominal value, and in particular a nominal measured value, from the group of variables time, in particular duration or time point of the supply of the conditioning radiation or x-ray radiation, operating time of the x-ray detector, radiation intensity (or radiation density, count rate, dose), in particular of the conditioning radiation or of the x-ray radiation.

Preferably, a calibration (described in more detail later) could be carried out with the aid of the nominal value and the supply of the conditioning radiation controlled or regulated on the basis of the completed calibration, for example on the basis of a plurality of target values (i.e. new nominal values to be aimed at successively). It should be emphasized in this context that in the simplest case it may be sufficient for x-ray imaging applications to perform a control function on the basis of the nominal value without further feedback of measured values for control purposes. In other words, one or more nominal values are specified or nominal measured values are acquired once, and thereafter the control function can be performed without the verification of further measured values.

With the aid of the nominal value, the supply of the compensation radiation can then be controlled or regulated for example such that aging effects of the semiconductor detector or of the radiation source are evaluated and if necessary compensated for by way of the control or regulation according to at least one embodiment of the invention. Preferably the generation of time-invariant (i.e. at least for the duration of a measurement sequence or x-ray detection measurement that is to be carried out) detector sensitivities can be aimed at, for example with the aid of time-invariant compensation radiation. Preferably, the distribution of space charges in the semiconductor material can also be kept constant with respect to time by additional generation of free charge carriers by way of the additional radiation.

In addition, it is, however, also possible to condition the semiconductor detector element with respect to specific measurement conditions, such as e.g. temperature, humidity, run time, current consumption of the semiconductor detector system, with the aid of the nominal value, such that these parameters are likewise taken into account in the control or regulation of the supply of the conditioning radiation, i.e. that the control and/or regulation is carried out as a function of the parameters, or are incorporated in the nominal value.

Particularly preferably, the method comprises a step for defining or specifying a nominal value such that the nominal value is variable and the variation can be effected in particular using a plurality of target values. As mentioned, the nominal value can be specified in a variable manner in particular within a measurement sequence or an x-ray detection measurement (i.e. for a temporally continuous duration in which a detection of x-ray radiation is to take place) or also specified variably for different measurement sequences or x-ray detection measurements.

The supply of the additional radiation or conditioning radiation is controlled or regulated with respect to time and/or with respect to the radiation density or radiation intensity or dose. Furthermore, the control or regulation can also be carried out with respect to the energy of the conditioning radiation. These parameters are mapped in control or regulating variables, such as for example a drive current for a radiation source. When control and/or regulation values assigned to corresponding control or regulating variables are changed, the supply of the conditioning radiation is also varied. For example, if the current intensity of the drive current is reduced, a radiation source is dimmed so that the intensity of the supplied conditioning radiation is decreased.

In other words, the control or regulation of the supply of the conditioning radiation can for example also include the regulation or control of the emission of the radiation of the radiation source.

Particularly preferably, the cited radiation source can be controlled with respect to one, more than one, or preferably all of the aforementioned parameters. In other words, a plurality of operating states can be set for the radiation source on the basis of control values or regulation values with respect to the parameters, which differ from a mere activation or deactivation of the radiation source. In this case a plurality of different values (i.e. the control or regulation values) can be set for the control or regulating variables. By taking one or more of the control or regulating variables into account it is possible to adapt the conditioning of the semiconductor detector element, as mentioned, to match the most diverse requirements, as will be explained in greater detail later.

Accordingly, an x-ray detector system having an x-ray detector for detecting radiation of an x-ray source is proposed within the scope of at least one embodiment of the invention. The x-ray detector has a direct-conversion semiconductor detector element, i.e. the detector element at least partially absorbs the x-ray radiation of an x-ray source that is to be detected and generates a detection signal based on the absorbed x-ray radiation. The detector is suitable in particular for use in x-ray imaging, for example in a computed tomography system, a SPECT system or a PET system.

The x-ray detector system according to at least one embodiment of the invention comprises a radiation source for supplying additional radiation to the semiconductor detector element and/or a control interface for driving a radiation source. The control interface can then be used for example for driving suitable radiation sources that are already present in an x-ray system (in particular a computed tomography system) to which the detector belongs, for the purpose of supplying the conditioning radiation directly or indirectly (via another control unit that is present). The already existing x-ray source can be for example a computed tomography system.

The x-ray detector system of at least one embodiment additionally includes a control unit which controls or regulates the supply of the additional radiation on the basis of a specified nominal value. It should be emphasized in this context that in the following description the term "control unit" not only includes the possibility of controlling the supply of the compensation radiation, but may also include the possibility of regulating the supply of the compensation radiation.

As already indicated, the nominal value can be variable. Particularly preferably, the control unit therefore has an input interface for specifying the nominal value such that the latter, which is variable with the aid of the input interface, can in each case be specified for an entire measurement sequence or also within a measurement sequence.

Other particularly advantageous embodiments and developments of the invention will become apparent from the dependent claims as well as from the following description, wherein the independent claims of one claims category can also be developed analogously to the dependent claims of a different claims category.

In a development of the method according to at least one embodiment of the invention, the radiation source includes at least one component from the group: UV light source, infrared light source, and light source for visible light. The light source preferably comprises one or more light-emitting diodes. The plurality of light-emitting diodes can also be what is known as a light-emitting diode cluster. Both the light-emitting diode and the light-emitting diode cluster can be controlled or regulated in terms of intensity or radiation density, or also the spectral distribution of the radiation or the wavelength of the emitted light. In the case of a plurality of light sources the control and/or regulation according to at least one embodiment of the invention can in particular also include the selection of one or more radiation sources from a number of available radiation sources.

The control and/or regulation can furthermore include for example the control of a current source, preferably a direct-current source, for driving the light-emitting diodes. This does not, however, preclude also using methods such as a technique known as pulse width modulation for controlling or regulating the light source, and controlling corresponding current sources on the basis of at least one embodiment of the invention. The respective light source can be in particular also a laser, a halogen lamp, a tubular fluorescent lamp, or similar light sources which if necessary are combined with a color filter or an attenuator device. All of these light sources can be, as mentioned, a controllable or regulatable light source.

Furthermore, it is not ruled out that the radiation source is also the x-ray source itself or that the radiation source includes an x-ray source. In other words, the x-ray source can likewise be controlled in such a way that a conditioning of the semiconductor detector element is achieved based on a specified nominal value. In particular the x-ray source can emit additional x-ray radiation as conditioning radiation which is not used for generating image information. In this case the control unit can for example make use of the cited control interface for driving the x-ray source in order to emit conditioning radiation.

In order in particular to enable the supply of the conditioning radiation to be regulated, the method preferably includes in addition a step in which a monitoring measured value corresponding to the nominal value is acquired. The term "corresponding" in this context means that the control or regulation is carried out on the basis of a correlation between nominal value and monitoring measured value. For example, the nominal value can be the operating time of a detector system. A correlation to an irradiation intensity that is to be set for the radiation source can then be determined for example as a function of the operating time, such that the monitoring measured value is the intensity of the supplied conditioning radiation. Preferably, however, the measurement quantity of the monitoring measured value corresponds to the magnitude of the nominal value. In this case the nominal value and the monitoring measured value can then relate for example to the intensity of the supplied conditioning radiation.

Particularly preferably, the x-ray detector system can have a monitoring unit for acquiring the monitoring measured value, which monitoring unit determines a monitoring measured value for example at a plurality of different time points, in particular before, during or after a detection of x-ray radiation that is to be detected e.g. in a computed tomography measurement. Particularly preferably, the control unit then has an input interface for receiving the monitoring measured value.

Particularly preferably, the monitoring unit is arranged outside of a primary beam path of the x-ray source to the semiconductor detector element, i.e. in particular on the narrow side of a substantially flat semiconductor detector element. In this way it is possible for example to mitigate or suppress radiation damage to the monitoring unit due to the x-ray radiation.

The monitoring unit can also include for example at least one shielding device to protect against the radiation of the x-ray source. Preferably this can take the form of a coating which is strongly absorbing or impermeable with respect to x-ray radiation. Examples of suitable candidate materials therefor include molybdenum, tungsten, lead, bismuth and platinum, or similar materials or coatings, such that it is nonetheless possible to position the monitoring unit close to the semiconductor detector element.

Preferably, the monitoring unit is made from a material which is particularly resistant to x-ray radiation. The x-ray detector and the monitoring unit are preferably integrated into the x-ray detector system in order to realize a particularly compact design.

In particular the deviation of the monitoring measured value from a nominal value, in particular from a target value, can be determined with the aid of the monitoring unit, and the supply of the conditioning radiation can be regulated or controlled based on the deviation. Preferably, a desired radiation intensity can be specified by the nominal value or target value. The supply of the conditioning radiation can then be controlled or regulated on the basis of the deviation of the monitoring measured value from the desired radiation intensity or from the nominal value.

In a preferred embodiment variant, a monitoring unit for acquiring the monitoring measured value has at least one component from the group comprising light sensor, x-ray sensor, semiconductor detector element of the x-ray detector, dosimeter, thermometer, luxmeter or evaluation electronics of the x-ray detector or a timekeeper or timer.

Possible monitoring measured values could then include for example the light intensity, the x-ray intensity, the light spectrum, a count rate of the x-ray detector or the strength or pulse shape of a photocurrent, a temperature, a radiation density or also a time or a time point.

Thus, the adaptation to the most diverse requirements for detection of x-ray radiation is made possible once again. In particular the monitoring unit can be incorporated in the x-ray detector system in addition to already existing components of the x-ray detector that are necessary for detecting x-ray radiation or for carrying out x-ray detection measurements.

The control or regulation can be implemented on the basis of a specified algorithm. The algorithm takes into account the specified nominal value and preferably also a target value, i.e. a modified nominal value. For example, a regulation can be effected on the basis of a PID algorithm (proportional-integral-differential control algorithm) and the control or regulation can be realized on the basis of a look-up table or correlation function which relates the nominal value to a control or regulating value which controls or regulates the supply of the conditioning radiation. For example, an intensity value of the conditioning radiation can be specified as the nominal value, to which intensity value a drive current value for LEDs serving as the radiation source is then assigned via a look-up table or a correlation function. The control or regulation is then effected for example by varying the drive current on the basis of the look-up table or correlation function.

In addition, however, the algorithm can also take into account one or more further input parameters for controlling and/or regulating the supply of the conditioning radiation, which can be forwarded for example also via an input interface of the control unit.

In this development of at least one embodiment of the invention, the algorithm can therefore be specified as variable. Preferably, the control unit then comprises one or more memories in which at least parts of the variable algorithm, for example the look-up table or the correlation function, can be stored. Particularly preferably, the input interface can also be embodied for forwarding a modified new algorithm to the control unit. In this way it is possible for example to adapt a conditioning of the semiconductor detector element to match different requirements which in particular demand a different type of regulation or control of the supply of the conditioning radiation with the aid of different control algorithms.

In a development of the method according at least one embodiment of to the invention, the supply of the additional radiation can be controlled or regulated based on the characteristics of an examination subject which is transradiated by way of the x-ray radiation that is to be detected. With regard to computed tomography, for example, a topogram measurement could be referred to in order to specify corresponding conditionings of the semiconductor detector element. A topogram measurement entails a quickly performed overview image acquisition on the basis of which for example a suitable measurement protocol is selected for a subsequent computed tomography image acquisition or image acquisition sequence. In particular, a nominal value can be derived or directly extracted based on the topogram measurement. For example, the derived or extracted nominal value can be a maximum count rate or a maximum sensitivity of the detector system. The supply of the conditioning radiation can then be controlled or regulated for example by intensity variation such that the maximum count rate or maximum sensitivity of the detector system is attained.

As already mentioned, it may be possible to take into account a plurality of input parameters in the algorithm or for controlling and/or regulating the supply of the conditioning radiation. In a development of the invention, the characteristics of the examination subject or one or more of the derived or extracted values mentioned in relation to the nominal value can also be taken into account in the input parameters of the cited algorithm.

In a development, the supply of the conditioning radiation can also be controlled or regulated based on the characteristic curve of the emission of the x-ray radiation by the x-ray source. Accordingly, this gives rise to the possibility of conditioning the x-ray detector in relation to the actually prevailing measurement conditions. For example, the supply of the additional radiation can be specified on the basis of the x-ray irradiation intensity, the spectrum used, the measurement protocol (in this case what this refers to, as is well-known, is the measurement program which controls a measurement fully automatically on the basis of specified parameters), individual preferred energies of the x-ray radiation, as a function of an operating mode of the device in which the x-ray detector is installed (for example appropriate to the dual-energy mode of operation of a computed tomography system). The control and regulation can be realized in particular on the basis of the characteristic curve of the attenuation of the x-ray radiation by the examination subject.

The cited parameters can in this case be taken into account as the nominal value or also as input parameters, for example in the calculation of a correlation function or for specifying the algorithm.

The characteristic curve of the supply of the conditioning radiation can be taken into account in particular at the time of the specification of the nominal value, such that, starting from a known conditioning, a flexible conditioning in relation to the most diverse requirements is once again produced in the operation of the detector.

Particularly preferably, the supply of the conditioning radiation is controlled and/or regulated based on a count rate drift. As already explained in the introduction, the count rate drift relates to the change with respect to time of a count rate of the detector or semiconductor detector element in question in relation to x-ray radiation that is to be detected in respect of a known or specified dose which can be based in particular on the variance of polarization effects with respect to time. Accordingly, the nominal value, for example the intensity or the spectrum of the conditioning radiation, can be specified based on a determined count rate drift which has been determined in turn e.g. from the history of the determined count rates, i.e. the preceding x-ray detection measurements or different conditionings with the aid of the radiation source.

Particularly preferably, the supply of the additional radiation can be controlled or regulated on the basis of one or more of the following variables: irradiation time, administered dose, detection signal, total operating time of the detector, current consumption of a semiconductor detector element, current consumption of a group of semiconductor detector elements, temperature or humidity. In other words, the radiation density of the conditioning radiation can be controlled and/or regulated for example as a function of how long the irradiation/conditioning has already lasted or what dose of x-ray radiation and/or conditioning radiation has been supplied to the semiconductor detector element in a specified time segment, or on the basis of the ambient conditions, such as temperature or humidity, which can likewise significantly influence the polarization or absorption of x-ray radiation. The current consumption of a semiconductor detector element or the current consumption of a group of semiconductor detector elements can furthermore deliver a direct pointer to the conditioning of the semiconductor detector element.

Furthermore, it is possible at the time of specifying the nominal value also to take into account for example variables which influence the introduction of new traps into the semiconductor detector material. This can also be taken into account with the aid of the evaluation of the total operating time of the detector for specifying the nominal value. For example, the intensity and/or duration of the conditioning can be controlled and/or regulated on the basis of the operating time or total operating time. In other words, an intensity and/or duration representing the nominal value is determined, and for example a drive current value for the radiation source and/or a drive time (duration) of the radiation source controlled and/or regulated, on the basis of the variable time.

Particularly preferably, the control and/or regulation is effected such that the additional radiation is supplied in a time window in which the x-ray source emits no x-ray radiation. Thus, for example, a specific conditioning of the semiconductor detector element can be set before or after an x-ray measurement. In particular when the characteristic curve of the x-ray measurement is such that no additional drift of the count rate is to be expected, this is a simple way specifying the conditioning of the semiconductor detector element. Accordingly, the possibility also arises to determine a monitoring measured value in the time window in which the additional radiation is supplied, while no corresponding monitoring measured value is determined either whenever the x-ray source emits no x-ray radiation.

Preferably, the supply of the additional radiation is controlled or regulated such that the intensity or the spectral distribution of the additional radiation is substantially constant, in particular during a given measurement section in which the x-ray radiation is to be detected. In this way it can be ensured for example that aging effects of the radiation source can be identified and compensated for and in addition a reliable back-calculation to count rates of the semiconductor detector element can be carried out. In particular the constant supply of the conditioning radiation can be checked with the aid of the acquisition of monitoring measured values.

In another preferred variant, the supply of the additional radiation is controlled or regulated in such a way that the measured current consumption of a semiconductor detector element and/or of a group of semiconductor detector elements of the x-ray detector (where the current consumption may be given by the sum of the additional radiation and the x-ray radiation) is substantially constant during a given measurement section in which the x-ray radiation is to be detected. Substantially constant, in the present context, means that a non-zero baseline level of the current consumption is constant, irrespective of whether x-ray radiation is supplied or not, and, starting from the baseline level, additional current pulses or charge packets which represent the actual detector signal are generated on the basis of the x-ray radiation. This is particularly useful when using quanta-counting x-ray detectors (described in greater detail later) in which the non-zero baseline level lies below threshold values which trigger a count. In this case, however, the current consumption of an individual semiconductor detector element can still vary above or around the baseline level with the image information conveyed via the x-ray radiation.

As explained in the introduction, x-ray detectors, specifically detectors for computed tomography systems which are based on directly transforming or directly converting semiconductor materials such as e.g. cadmium telluride or cadmium zinc telluride, are subject to an instability with respect to time in the generation of a detection signal for x-ray radiation. In particular, the detection signal varies with time, given actually constant excitation by way of x-ray radiation. This is undesirable and leads to artifacts in the imaging, with the result that with their current performance the detectors can be used at the present time only with difficulty in imaging methods based on x-ray radiation. By illuminating the semiconductor detector material it is possible to generate so many free charge carriers that a stable state is established and the polarization effect explained in the introduction can be neutralized or stabilized. As a result, a stabilized measurement signal or detector signal required for the measurement of x-ray radiation can be ensured, thus enabling the use of such detectors also in medical imaging. However, when a sensor material or semiconductor detector element is used whose response behavior is stabilized by way of external illumination, uncontrolled changes in the illumination, e.g. due to aging, failure, temperature fluctuations, radiation damage and the like can negatively affect the stability of the signal. This in particular can be prevented with the aid of the invention.

Furthermore, the count rate drift mentioned in the introduction is particularly problematic in the case of counting x-ray detectors, i.e. in the case of detectors which determine a count rate for x-ray quanta on the basis of one or more threshold values. This change in the detection accuracy, which is difficult to predict with regard to time, also leads to particularly strong imaging artifacts. With the aid of the invention the possibility is created to recognize and in particular to prevent this undesired change in the stabilization or conditioning.

FIG. 1 shows, in a schematic illustration, a computed tomography system 1 having an x-ray source 10 which emits x-ray radiation R in the direction of an x-ray detector system 200.

Figure 6:
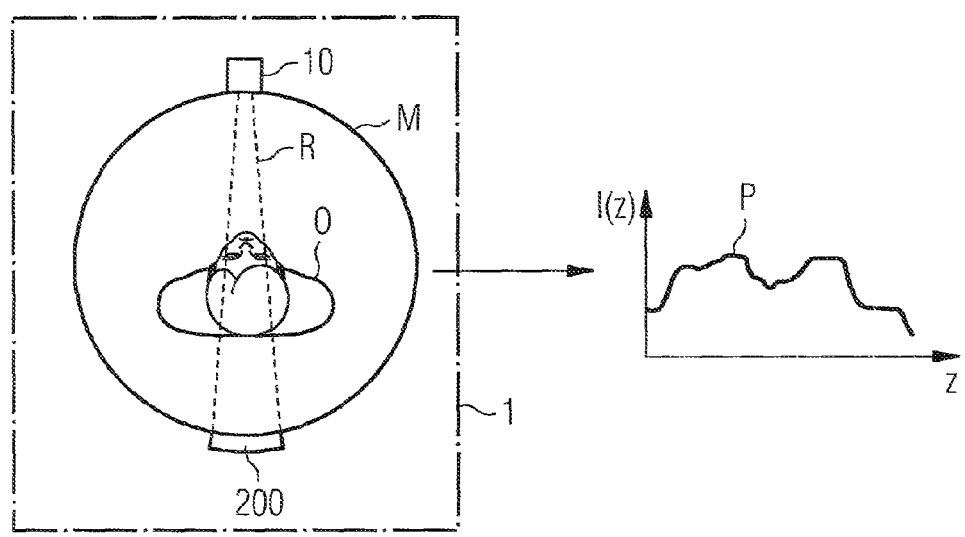
FIG. 6 shows an example embodiment for determining a nominal value on the basis of the characteristics of the examination subject.

In this case the CT system 1 has a conventional scanner in which the detector system 200 having a detector 100 and an x-ray source 10 disposed opposite the detector 100 rotate around a measurement chamber (as also shown in FIG. 6) on a gantry. Located in front of the scanner is a patient support device or patient table (not shown), the upper part of which can be displaced, with a patient or test subject or examination subject disposed thereon, relative to the scanner in order to move the examination subject relative to the detector system 200 through the measurement chamber. The scanner and the patient table are controlled by way of a control device (not shown) from which control data is sent via a conventional interface in order to drive the system in the conventional manner in accordance with specified measurement protocols. Basically, however, the method according to the invention can also be used on other CT systems, e.g. having a detector forming a complete ring.

The raw data acquired by the detector 100 is transferred to a measurement data interface of the control device. The raw data is then processed further in an image reconstruction device realized in most cases in the form of software on a processor in the control device. The image reconstruction device has a raw data interface for importing the x-ray CT datasets. A reconstruction is then performed for the data in order to generate image data. The finished computed tomography image data is then transferred to an image data interface which then stores the generated image data for example in a memory of the control device or outputs the data in the usual manner onto the screen of the control device or feeds the data via an interface (likewise not shown) into a network connected to the computed tomography system, for example a radiological information system (RIS) or stores the data in mass storage devices available there or outputs corresponding images on printers connected there. The data can also be processed further in any desired manner and then stored or output.

In addition to the already described x-ray detector 100, the x-ray detector system 200 has a plurality of radiation sources 210a and 210b for conditioning the x-ray detector 100. The x-ray detector 100 is in this case constructed as a so-called hybrid detector system, i.e. it has semiconductor detector elements 150a, 150b which differ in their starting semiconductor material (i.e. e.g. the wafer material) from the starting semiconductor material of an evaluation electronics circuit which serves for evaluating a detection signal of the semiconductor detector element 150a, 150b. It is therefore possible to position the evaluation electronics and the x-ray absorbing semiconductor detector element 150a, 150b independently from one another or to separate them in space so that under certain conditions advantages in terms of the longevity and maintenance of the components in question can be achieved. For example, a simple retrofitting of the detector system with additional components could be made easier in this way, with the result that advantages can be achieved with this design also with regard to the integration of the below-described invention.

In the example embodiment shown, the x-ray detector 100 is constructed as a stack of components. Starting from a substantially flat common substrate 180, a plurality of evaluation electronics circuits, called ASICs (Application-Specific Integrated Circuits), 160a, 160b are arranged in succession in the component stack (i.e. on the substrate) in a common plane of the component stack. The ASIC is an integrated circuit which is specifically embodied for evaluating a detection signal of one or more of the semiconductor detector elements 150a, 150b. In the example embodiment shown, following the ASIC 160a, 160b in the component stack (in the direction of the x-ray source), a discrete semiconductor detector element 150a, 150b is assigned to each ASIC 160a, 160b. The merely schematic illustration includes a spatially separated construction configuration of the discrete semiconductor detector elements 150a, 150b.

Going beyond the fidelity to detail of the schematic illustration, however, a plurality of the discrete semiconductor detector elements 150a, 150b are preferably arranged, adjoining one another in each case, in a contiguous starting material, for example in a contiguous semiconductor layer, in particular in a matrix-like structure.

In this configuration the ASICS can be completely covered by the semiconductor detector element 150a, 150b, such that the semiconductor detector element 150a, 150b covering the ASIC 160a, 160b, respectively, simultaneously forms an effective protection device against incident x-ray radiation R for the respective ASIC 160a, 160b.

This is achieved in a synergistic manner in that each of the semiconductor detector elements 150a, 150b is embodied to absorb incident x-ray radiation R without a preceding photochemical conversion process. These are what are called direct-conversion semiconductor detector elements 150a, 150b, which in the present example embodiment are fabricated from cadmium zinc telluride (CZT). Each of the semiconductor detector elements 150a, 150b is connected to a number (preferably two to four) of field electrodes (not shown) with the aid of which an electric field can be impressed onto the respective semiconductor detector element 150a, 150b. Located between the field electrodes is the detection zone of the semiconductor detector element 150a, 150b, which essentially represents a pixel of the x-ray detector 100. The substantially flat semiconductor detector element 150a, 150b (i.e. it can be inscribed into a flat cuboid and touches each side of the cuboid), which has a narrow side and a flat side which faces toward the direction of incidence of the x-ray radiation R, is operated in the example embodiment as a depleted cadmium zinc telluride diode.

Incident x-ray radiation R is absorbed in the semiconductor detector element 150a, 150b, where it generates a number of conduction electrons and holes as a function of the respective energy of the x-ray quantum. On account of the electric field, it drifts to the field electrodes, where it produces a measurable detection signal or a measurable detection pulse. The measurable detection pulse can be acquired as a current or voltage signal with the aid of the ASIC 160a, 160b, evaluated, and in particular digitized so that the signal can be supplied for further processing, i.e. for the reconstruction of image data in the example embodiment. This possibility of evaluating current or voltage signals or the possibility of digitization can advantageously be used in order for example to measure or analyze not only signals of the semiconductor detector elements 150a, 150b, but also other current or voltage signals. As is explained below, these can be for example also the signals from light sensors or other components. In that respect the ASICs 160a, 160b are constructed here in such a way that they simultaneously also represent monitoring units 160a, 160b, with the aid of which a monitoring measured value Ma, Mb (described in greater detail later) can be acquired, measured and also analyzed, in particular digitized.

In the example embodiment shown, the ASIC 160a, 160b is in each case embodied to determine a count rate for x-ray quanta. In other words, the detector is what is termed a "counting" or "photon-counting" or "quanta-counting" x-ray detector 100, with one or more energy thresholds (i.e. threshold values for the measured current or voltage signal) being specified. On the basis of the energy threshold, a counter can then be incremented in order thereby to be able to determine the count rate for x-ray quanta, i.e. the number of x-ray quanta per unit time, which exceed the specified energy threshold.

However, the electric field generated with the aid of the field electrodes is modified in the semiconductor detector element 150a, 150b as a function of time, which means that in principle there exists the risk that the corresponding count rate may be determined with error. As explained in the introduction, one cause for the time-dependent change in the electric field is the effect known as polarization, i.e. the variable formation of space charges over time.

In order to be able to influence the change in the electric field over time, the x-ray detector system has radiation sources 210a, 210b which in the example embodiment are in each case formed by a plurality of infrared light-emitting diodes. Using a plurality of diodes of similar type gives rise among other things to the possibility, as will be explained in more detail later, of increasing the fault resilience of the radiation sources 210a, 210b. The light-emitting diodes supply the semiconductor detector element 150a, 150b with a conditioning radiation K, likewise explained in the introduction, with the aid of which the time-dependent change in the electric field can be modified.

Toward that end, the x-ray detector 100 has a further layer which is arranged downstream of the detector element 150a, 150b in the component stack (again in the direction toward the x-ray source). This layer is embodied as a light conductor 120 and is largely transparent to incident x-ray radiation R. Accordingly, the light conductor 120 can be arranged in the beam path of the x-ray source 10 to the semiconductor detector element 150a, 150b without exerting a significant influence on the determined count rate. On the side facing away from the semiconductor detector element 150a, 150b and facing toward the incoming x-ray radiation R, the light conductor 120 comprises a reflection layer 110 which reflects the conditioning radiation K of the radiation sources 210a, 210b and thereby optimizes the conduction of light. It should be emphasized in this context that the reflection layer 110 is likewise largely transparent to the radiation R of the x-ray source 10. The radiation sources 210a and 210b arranged outside of the beam path of the x-ray source 10 couple the conditioning radiation K, preferably at a suitable angle, into the light conductor 120. The arrows depicted in FIG. 1 schematically indicate only the main emission direction of the radiation sources 210a and 210b, though these may have a different emission characteristic, e.g. cone-shaped.

This coupling-in is indicated only schematically in the example embodiment; in particular the radiation source 210a, 210b can be arranged in such a way that the conditioning radiation K is coupled in its entirety into the light conductor 120.

The conditioning radiation K is distributed with the aid of the light conductor 120 substantially uniformly over the flat side of the semiconductor detector elements 150a, 150b, such that a location dependence of the supply of the conditioning radiation K for one or more of the semiconductor detector elements 150a, 150b or for the detection zones can be avoided. For that purpose, special coupling-out structures (not shown) are installed in the reflector layer 110 which increase the portion of the conditioning radiation K reflected in the direction of the surface of the semiconductor detector element 150a, 150b with increasing distance from the radiation source 210a, 210b, such that the radiation density or intensity of the conditioning radiation impinging on the semiconductor detector element 150a, 150b is substantially constant in space.

As indicated by the dashed line, the x-ray source 10 can also be used in the example embodiment to supply conditioning radiation K to the semiconductor detector element 150a, 150b. In this case the conditioning radiation K of the x-ray source 10 is different from the conditioning radiation K of the radiation sources 210a and 210b not only in terms of the type of radiation, but in particular also in terms of its energy and its intensity. Accordingly, different conditionings of the semiconductor detector elements 150a, 150b can be achieved with the aid of the different conditioning radiation K and the different conditioning radiation sources, x-ray source 10 and light-emitting diodes in the example.

This can be accomplished for example by way a control unit 300. In this case the x-ray detector 100 has a control unit 300 which controls and regulates the supply of the conditioning radiation K to the semiconductor detector elements 150a, 150b with the aid of control signals CS. The control signals CS are in this case forwarded to the radiation sources 210a, 210b (or optionally to the x-ray source 10) and can directly correspond to already cited control or regulating variables, or replicate these indirectly. As shown in FIG. 1, the control unit 300 is also arranged integrated in one of the ASICs 160a or one of the monitoring units 160a, 160b and can therefore advantageously use circuits and functions of the ASIC or also data present within the ASIC. In this case, as indicated by the dashed block in the ASIC 160b, the control unit 300 can be realized in each of the ASICs or also be distributed over a plurality of ASICs.

In the case of a plurality of semiconductor detector elements 150a, 150b, the supply of the conditioning radiation K can also be controlled or regulated individually for each of the semiconductor detector elements 150a, 150b. This offers in particular the advantage that the conditioning of large-area detector systems 200 can be optimized. For this purpose a respective dedicated control unit 300 can also be assigned to each ASIC.

Alternatively or in addition, the supply of the conditioning radiation K can also be controlled or regulated by way an additional electronics circuit which is present independently as a so-called "module backplane" for the detector system 200. The module backplane typically comprises programmable logic units such as FPGAs and/or storage elements which can already assume control tasks in respect of the x-ray detector. The control unit 300 can then be arranged integrated into the "module backplane" and likewise use already available circuits or functions of the "module backplane" such as e.g. FPGAs and/or storage elements. These circuits and functions then have a multiple use. This is a particularly advantageous arrangement when a central control unit 300 is to be used for a plurality of semiconductor detector elements 150a, 150b, and furthermore a retrofitting of the invention into already existing detector systems can also be facilitated in this way.

The control unit 300 possesses input interfaces 310a, 310b, 310c which receive a nominal value Ta, Tb, Tc from a nominal value storage unit 400 or else a monitoring unit 160a, 160b and make it available to the control unit 300. The supply of the conditioning radiation K to the semiconductor detector elements 150a, 150b is controlled or regulated on the basis of the nominal values Ta, Tb, Tc.

Preferably, the nominal value Ta, Tb, Tc is in this case determined by measurement, in particular before an x-ray detection measurement, the result of which is to be supplied for further use, is performed with the aid of the detector 100. A correspondingly determined nominal value Ta, Tb, Tc can for example be stored in the nominal value storage unit 400. The nominal value storage unit 400 can be for example a measurement protocol storage unit of the computed tomography system in which one or more measurement protocols for performing a computed tomography measurement are stored. The nominal value Ta, Tb, Tc can also be a measured value determined in the course of the detection of the x-ray radiation R or of the supply of the conditioning radiation K, in particular with the aid of one or more of the monitoring units 160a, 160b, 160c.

In the example embodiment, the intensity of the conditioning radiation K is measured for example with the aid of a light sensor 160c, which in turn represents a monitoring unit 160c. The light sensor 160c is mounted in such a way that it measures the effective irradiation intensity impinging on the semiconductor detector element 150a, 150b in an optimal manner. As FIG. 1 shows, the light sensor 160c is installed to the side of the semiconductor detector element 150a, 150b, i.e. in particular on or at its narrow side, so that it casts no shadow onto the semiconductor detector element 150a, 150b.

The light sensor 160c is therefore arranged outside of the primary beam path of the x-ray source 10 to the semiconductor detector element 150a, 150b. Furthermore, it is additionally protected mechanically against scattered x-ray radiation R. This mechanical protection nonetheless ensures an effective measurability of the illumination intensity. A corresponding protection device or shielding device of the light sensor can for example consist in the use of molybdenum, tungsten, lead, bismuth and platinum. A corresponding protection layer could be assigned to one or more of the light sensors 160*c*.

In spite of its protection against scattered x-ray radiation R, the light sensor is furthermore constructed from a material which is maximally insensitive to the x-ray radiation R. For example, a material can be used which is largely transparent to x-ray radiation.

Going beyond the illustration in FIG. 1, the light sensor could be integrated in the already cited ASIC. This enables the illumination intensity to be acquired directly in the ASIC. In other words, the illumination intensity is measured in particular directly with the aid of the additionally installed light sensor. Measured directly means in this case that the measured value is the measured value of a dedicated light sensor having no other function than for example to measure the intensity of the conditioning radiation. A plurality of independently dedicated sensors could be present in order for example to measure directly the time or duration of the supply of radiation, in particular the conditioning radiation or the wavelength or the spectrum of the radiation (i.e. in particular of the conditioning radiation).

In addition, the semiconductor detector element 150*a*, 150*b* in conjunction with the associated evaluation electronics (i.e. the ASIC) can also represent a sensor for the supply of the conditioning radiation, and in particular a light sensor.

For example, given the cited circuit configuration of the semiconductor detector element 150*a*, 150*b* with field electrodes, the irradiation intensity can be determined from the electric current flowing through the semiconductor detector element 150*a*, 150*b*. The electric current can to that end be measured via the field electrodes or the voltage supply of the semiconductor detector element 150*a*, 150*b* and digitized. This represents an indirect measurement of the illumination intensity within the meaning of the invention, since the irradiation intensity is determined with the aid of a "light sensor" which is not a dedicated light sensor, i.e. also fulfills other functions during the detection of x-ray radiation.

It is also possible to measure the current by way of the ASIC 160*a*, 160*b* which is directly coupled to the semiconductor detector element 150*a*, 150*b*. This is particularly advantageous because the ASIC 160*a*, 160*b* already contains circuits for measuring and digitizing analog signals and in addition, as already mentioned, offers the possibility of a direct integration of the control unit 300, i.e. of circuits for the dynamic regulation and control of the illumination intensity.

In an example embodiment, the supply of the conditioning radiation can then be controlled or regulated for example with the aid of the current consumption of a group of semiconductor detector elements 150*a*, 150*b*. The current consumption could then be measured during the supply of the conditioning radiation directly via the voltage supply of the field electrodes and represents a nominal value which specifies a baseline level of the current consumption. The radiation intensity is controlled in the example embodiment in such a way that the baseline level is substantially constant. In other words, the baseline level of the current consumption is attained independently of a performed x-ray measurement. It can therefore be assumed that the semiconductor detector element is conditioned virtually constantly.

When the described "quanta-counting" detector is used, the conditioning radiation can then be controlled in such a way that the baseline level of the current consumption lies below threshold values for determining a count rate. Accordingly, a specific, and potentially computationally intensive, consideration of the characteristic curve of the control of the conditioning can be avoided in the evaluation of the detection signals.

Figure 2:
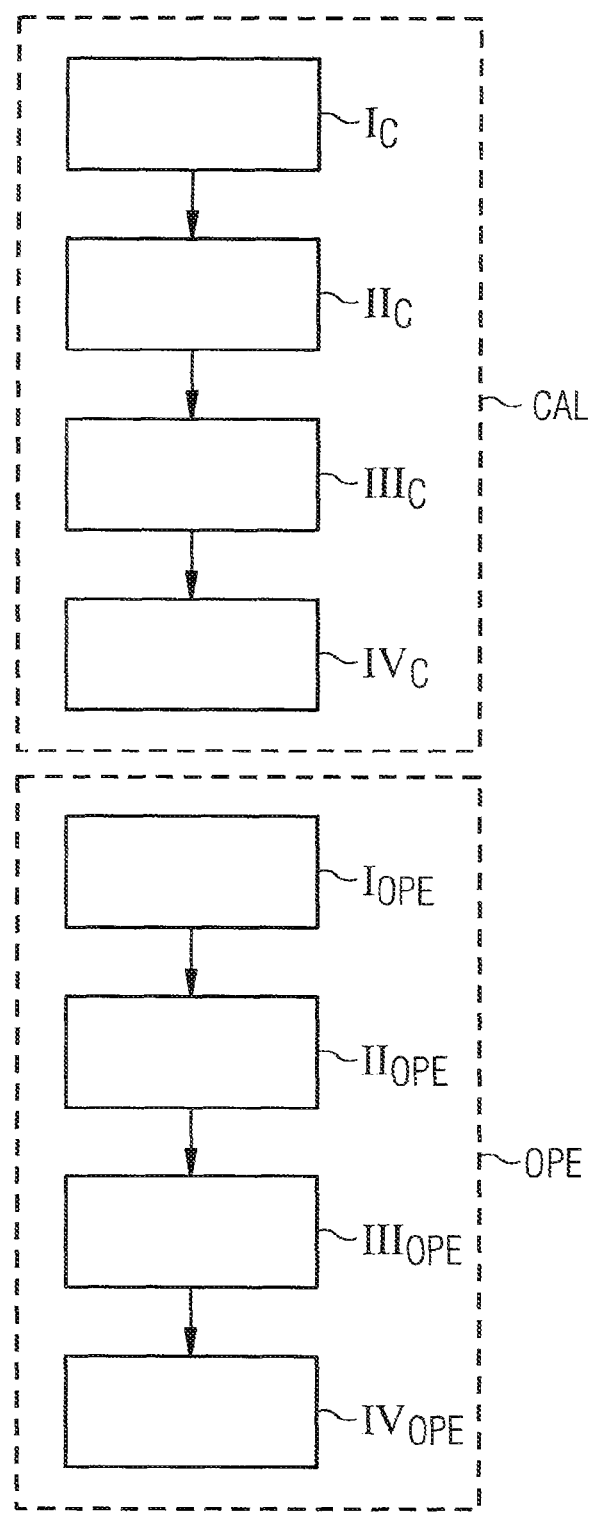
FIG. 2 shows a flowchart of an example embodiment of an x-ray detection method for detecting x-ray radiation which comprises calibration steps and operating steps.

FIG. 2 next shows a further method for detecting x-ray radiation which can be carried out with the aid of the detector system 200 illustrated in FIG. 1. In particular the significance of the nominal value for controlling and regulating the supply of the conditioning radiation is explained with reference to an example embodiment, and in particular the variation of the nominal value relative to a plurality of different target values.

With the aid of the control and/or regulation it can be aimed to ensure a maximally constant illumination intensity with respect to time, so that for example problems occurring over the long term, such as degeneration or failure of the radiation sources, can be identified and also compensated for.

The method for detecting x-ray radiation explained with the aid of FIG. 2 in this case subdivides the method steps into two groups. A first group comprises calibration steps CAL for specifying a nominal value, and a second group has steps which reveal the control or regulation of the conditioning radiation on the basis of the nominal value, and accordingly describes operating steps OPE of the detector system. During operation with the operating steps OPE, the nominal value can be varied in particular in order to achieve a plurality of different target values.

The calibration steps CAL of the first group therefore then subsequently enable the operation and in particular the control and regulation of the supply of the conditioning radiation in a plurality of operating steps OPE according to the second group.

In a first step IC, the radiation source is initially switched on in order to supply the semiconductor detector element with a specific conditioning radiation. Step IC therefore describes the variation of a control value which controls the supply of the conditioning radiation to the semiconductor detector element from 0 to a specified value. The IR LED light source described in FIG. 1 can e.g. be driven initially at a specific current intensity (corresponding to an mA value).

In a step IIC, the intensity of the conditioning radiation supplied to the semiconductor detector element can be measured (e.g. with the aid of the ASIC, as described with reference to FIG. 1), in particular also via (indirect) corresponding variables such as the current consumption of the semiconductor detector element, for example.

Insofar as it is a question of keeping the conditioning radiation constant with respect to time, the intensity value measured in step IIC can in the remainder of the method form a nominal value or nominal measured value. Thus, step IIC then serves for determining a nominal value on the basis of which the supply of the conditioning radiation is controlled.

In a further calibration step IIIC, a correlation or correlation function is then determined between the current intensity (i.e. the mA value, in other words the control value of a control variable which controls the supply of the conditioning radiation) at which the radiation source is operated and the intensity value measured by way of the ASIC, i.e. a type of ACTUAL value which indicates how much conditioning radiation is actually supplied to the semiconductor detector element.

In the case of a simple correlation it may be sufficient, as described, to refer to a single measured value or ACTUAL value in order to determine the correlation. For more complicated correlations, steps IC and/or IIC can be repeated if necessary for other control values and measured values, in other words the control values can be varied.

In a fourth optional calibration step IVC, as indicated by the dashed line, a look-up table (also referred to as a correlation table) can be generated which, on the basis of the determined correlation, assigns a specific control value (in this case the current value for driving the LED light sources) to a measured value (in this case the measured intensity) of the conditioning radiation. This assignment is carried out in the look-up table for a plurality of control values.

The ACTUAL values stored in the look-up table (which can be the measured values determined directly during the calibration and/or also values interpolated therebetween) can therefore be used during subsequent operation also as potential nominal values or target values (i.e. varied or modified nominal values) in order to determine the associated (nominal) control values. Accordingly, the look-up table therefore also contains a plurality of assignments of nominal values or target values (i.e. modified nominal values) to control values that were determined on the basis of the correlation.

Steps IC to IVC, in other words the calibration steps CAL, can in this case be initiated by the control unit mentioned with reference to FIG. 1, or can be performed with the aid of the control unit. In particular the calculations or measurements can be initiated or where necessary performed with the aid of the control unit. It is, however, also conceivable for the calibration steps CAL to be performed independently of the control unit.

If such a calibration is performed repeatedly, an aging of the radiation sources can preferably also be identified at an early stage on the basis of changes in the ACTUAL values (or potential nominal values) in comparison with preceding measurements. An uncontrolled change in the supply of the conditioning radiation is prevented in this way. A warning in this regard can then be output so that for example a replacement of the radiation sources is initiated before the failure of the radiation sources causes a degradation in image quality or even a failure of the tomography system or of the device used.

The look-up table can then be forwarded for example to the control unit preferably via one of the input interfaces mentioned with reference to FIG. 1, so that a control algorithm of the control unit operates for the purpose of controlling the supply of the conditioning radiation on the basis of the look-up table. In particular it should be emphasized that calculating the correlation function multiple times for identical points of the correlation can be avoided with the aid of the look-up table.

As already indicated, step IVC can, however, also be performed merely optionally. In this case the correlation, or correlation function on the basis of which the associated control value can subsequently be determined for each nominal value or target value (i.e. desired ACTUAL value), can be forwarded to the control unit so that the control unit will control the supply of the conditioning radiation on the basis of the determined correlation function.

In the example embodiment, the supply of the conditioning radiation is controlled with the aid of the operating steps OPE.

After the look-up table or the correlation function has been determined, the operation of the detector system can then proceed such that a target value or nominal value for an effective radiation intensity is specified which ensures a specific conditioning of the semiconductor detector element. This takes place in a first step IOPE.

In a further step IIOPE, the supply of the conditioning radiation is controlled on the basis of the look-up table or correlation function (in the below-described case a look-up table is assumed; the method executes analogously with a correlation function) in such a way that a specific effective intensity of the conditioning radiation corresponding to the target value is achieved.

For this purpose an mA value corresponding to the specified radiation intensity is taken from the look-up table and in a third step IIIOPE the radiation source is driven at the mA value such that an effective irradiation intensity corresponding to the target value is achieved.

The target value, i.e. in this case the intensity of the conditioning radiation, can, as mentioned, be constant during the operation of the detector system.

The quality of the x-ray imaging in particular can be improved as a result of the temporally uniform, constant and therefore better illumination. This is based for example on the fact that the conditioning of the semiconductor detector element is to a large extent invariant with respect to time and is therefore known. A degeneration of the radiation sources can consequently be compensated for, since the control is effected on the basis of a measured value.

This means for example that it is possible to use relatively inexpensive standard radiation sources that are not required to be of exceptionally high quality, since corresponding deviations can be corrected with the aid of the control and also regulation of the conditioning radiation.

The advantage of a known conditioning can also be retained in the case of a dynamically modified conditioning, in other words a dynamically varied supply of the conditioning radiation. If the intensity of the conditioning radiation is known, then the conditioning of the semiconductor detector element is also known or can be determined, such that the target value, in other words the intensity of the conditioning radiation aimed at in each case, can be varied dynamically without sacrificing information relating to the conditioning of the semiconductor detector element.

Thus, one of the advantages of at least one embodiment of the invention can also be the adaptability to different operating requirements of the detector system, without negatively affecting the quality of the x-ray imaging and in particular of the computed tomography measurement.

For this reason, according to a further operating step IVOPE in the method, steps IOPE to IIIOPE can be repeated each time there is a change to the nominal value. As soon as a new desired intensity of the conditioning radiation, i.e. a new target value, is specified in step IOPE, a corresponding mA value is determined on the basis of the look-up table, and the LED light source is driven by way of an operating current of the determined mA value (IIOPE, IIIOPE).

Furthermore, the method can also be extended to the effect that the supply of the conditioning radiation is not only controlled, but also regulated.

As already described in the example embodiment, the effective intensity of the conditioning radiation is determined in step IIC, preferably with the aid of the ASIC. In irradiation pauses, i.e. whenever no x-ray radiation is evaluated with the aid of the ASIC, it can then be checked whether the supply of the irradiation also corresponds to the specified nominal value. To that end, the intensity of the conditioning radiation can be measured as a monitoring measured value (or current ACTUAL value), for example with the aid of the ASIC, as described with reference to FIG. 1, and compared with the nominal value. In the event of a deviation, a correction to the mA value can be regulated accordingly until the nominal value is reached. In this way a regulation of the supply of the conditioning radiation can be realized with the aid of a monitoring value corresponding to the nominal value. An aging of the light sources for example can then also be identified on the basis of the monitoring measured value, with the result that a warning is issued, as described.

Furthermore, a temperature dependence of the illumination intensity of the radiation sources can be detected with the aid of a monitoring measured value or the described calibration and corrected, or a failure of a radiation source can be detected and compensated for by proportionally higher intensity of further radiation sources that are possibly available.

FIG. 1 in this case provides further pointers to ways and means in which the described methods for controlling and regulating the conditioning radiation may be developed.

In the example embodiment of the detector system 200 according to FIG. 1, as mentioned, a plurality of monitoring units 160*a*, 160*b*, 160*c* are shown which are able to determine a monitoring measured value Ma, Mb, Mc (in particular the intensity of the conditioning radiation K). These monitoring measured values Ma, Mb, Mc can then be forwarded in turn to the respective input interface 310*a*, 310*b*, 310*c* so that for example the control can be effected on the basis of the deviation of the monitoring measured value Ma, Mb, Mc from the nominal value Ta, Tb, Tc. If external monitoring units 160*c*, such as the light sensor for example, are used for this, a control or regulation can also be effected during an x-ray detection measurement. For example, the light sensor can be used as monitoring unit 160*c* in place of the ASIC in the method described with reference to FIG. 2.

In addition to taking into account the deviation of the monitoring measured value, other regulating or control algorithms, which may be based in particular on a complex control and regulation model having a plurality of input parameters, also come into consideration.

In the example embodiment, in addition to the intensity of the conditioning radiation, the light sensor or the semiconductor detector elements (e.g. for x-ray radiation as conditioning radiation) can also detect its spectral distribution or determine or measure the energy (wavelength) of the conditioning radiation. These measured values can also be forwarded as monitoring measured values Ma, Mb, Mc to the control unit 300, or serve as nominal value Ta, Tb, Tc. Furthermore, the control or regulation of the supply of the conditioning radiation can also include adapting the monitoring units 160*a*, 160*b*, 160, and in particular the light sensor, to match the spectrum of the radiation source. For example, this could include the selection of a light sensor, i.e. a light sensor which can detect substantially red light can be arranged such that it detects the radiation of a red radiation source. In addition, the adaptation may also consist in a choice being made for example between the ASIC and other light sensors, in particular as a function of the available or used radiation source.

Figure 3:
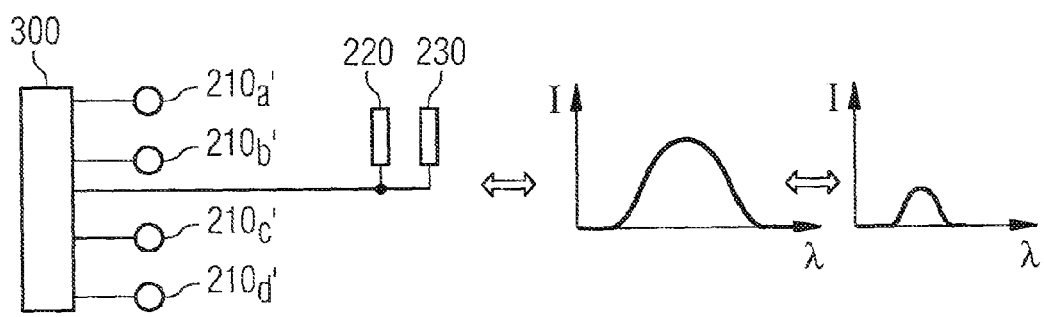
FIG. 3 shows an example embodiment of the control of a plurality of different light sources which can be controlled or regulated with respect to the intensity and the spectral distribution of the emitted radiation.

FIG. 3 shows in greater detail how the radiation sources may be controlled or regulated. In the illustrated example embodiment, various light sources 210*a*', 210*b*', 210*c*', 210*d*' serving as radiation sources for the conditioning radiation are connected to the control unit 300. One light source 210*a*' is formed by way of an LED cluster which comprises both LEDs that emit light in the visible range and LEDs that emit light in the UV or IR range. The use of LEDs is therefore particularly beneficial, since by the nature of their construction LEDs are particularly failure-proof and by virtue of their dimensions can be integrated for example into the detector system. Furthermore, LEDs in particular offer the possibility of serving as redundant radiation sources which can be activated as and when needed in order to supply the conditioning radiation. For this reason in particular, the control and also regulation in the case of a plurality of light sources also includes selecting a number of light sources that are used for supplying the conditioning radiation.

In addition, a further light source 210*b*, which in this case is formed by way of a halogen lamp, is connected to the control unit 300. Connected downstream of the halogen lamp in the optical path of the conditioning radiation to the semiconductor detector element is a spectral filter unit 220 whose spectral bandwidth is controllable.

In addition, an attenuator device 230 is likewise connected downstream of the filter device 220, and consequently also of the light source 210*b*', in the optical path of the conditioning radiation to the semiconductor detector element. With the aid of the controllable attenuator device 230, the light of the radiation source 210*b*' can be controlled or regulated with respect to the intensity of the additional radiation supplied to the semiconductor detector element. Accordingly, the radiation source, which is formed by the combination of filter unit 220, attenuator unit 230 and light source 210*b*', can be controlled or regulated with respect to the spectral distribution of the conditioning radiation and the intensity of the conditioning radiation, as is likewise indicated in FIG. 3. In the two diagrams shown on the right, which describe the spectral distribution (i.e. over the wavelength λ) of intensity values I of the conditioning radiation, it can be seen how, for example, the wavelength range in which the conditioning radiation is emitted and the intensity of the emitted conditioning radiation can vary.

A further light source 210*c*' is formed by a fluorescent lamp which is likewise connected to the control unit 300. The fluorescent lamp emits both conditioning radiation in the visible wavelength range and conditioning radiation in the UV wavelength range. Accordingly, a fluorescent lamp forms a simple possibility for a radiation source having a particularly wide radiation spectrum for the conditioning. A radiation source which is controllable over a particularly wide spectral range can therefore be constructed for example in combination with the already cited filter units (or also attenuator units).

A light source 210*d*' formed by a laser is also connected to the control unit 300. The laser emits a substantially monochromatic conditioning radiation, such that a special conditioning can be reliably set with the aid of the laser.

The use of a plurality of lasers as radiation sources is not excluded here, and in particular it is also not ruled out that the cited light sources 210*a*', 210*b*', 210*c*', 210*d*' are present in multiples for the purpose of supplying the conditioning radiation.

Figure 4:
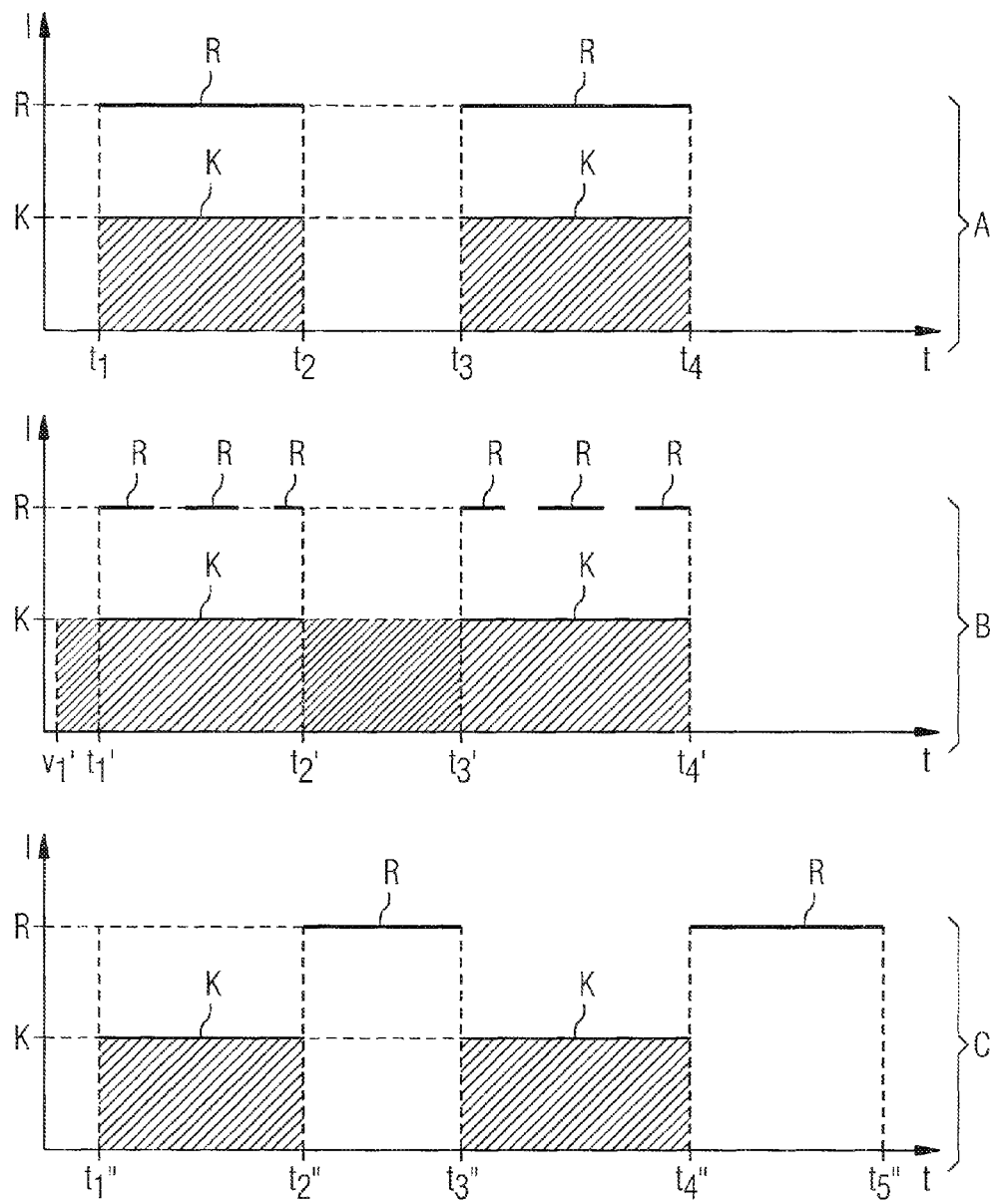
FIG. 4 shows a time scheme which describes different variants for the control of the supply of conditioning radiation with respect to time.

It is furthermore indicated in FIG. 4 how the supply of the conditioning radiation can be controlled and/or regulated with respect to time. Shown here in each case is the intensity I of the conditioning radiation K and the x-ray radiation R used for the imaging, plotted over time t.

As already mentioned, it is possible with the aid of the invention, inter alia, to adapt the x-ray detector system to match different requirements in particular in relation to x-ray imaging.

As a function of the irradiation requirements described in greater detail below, the supply of the conditioning radiation can be controlled or regulated with respect to time by switching or choosing between a plurality of temporal control or regulation variants. Furthermore, it is also possible to use an arbitrary combination of the temporal control or regulation variants shown in FIG. 4.

For example, in a variant A for the temporal control or regulation, the x-ray source emits x-ray radiation R in a first time period which lasts from time point t1 to time point t2. During this time period, conditioning radiation K is also supplied to the semiconductor detector element. This is also the case in the time period which lies between time points t3 and t4. In the time period between time points t2 and t3, however, the x-ray source emits no x-ray radiation. Accordingly, the detector is only conditioned when the x-ray radiation also impinges on the detector, such that a known conditioning of the semiconductor detector element is given during the x-ray measurement. This can be achieved in particular by way of the temporal control of the radiation sources that emit no x-ray radiation.

Alternatively, as in variant B for example, a continuous irradiation can be performed with conditioning radiation over several measurement sequences. In contrast to variant A, in which, as mentioned, the supply of the conditioning radiation is stopped when the x-ray radiation is switched off, in variant B the supply of the conditioning radiation can be controlled or regulated with respect to time in such a way that during several x-ray measurements or measurement sequences that are to be performed, which can also include pauses, uninterrupted conditioning radiation is supplied. This is the case here for example in the entire time segments from time point t1' to time point t4'. In this case an x-ray detection measurement is carried out only in the respective time segments between time points t1' and t2' and t3' to t4'. The last-mentioned time segments therefore relate to a number of measurement sequences for providing a computed tomography image acquisition.

Furthermore, the supply of the conditioning radiation in variant B can also be carried out with a lead time before the first measurement sequence, e.g. in the morning before the device is first put into operation. In a time segment lasting from time point v1' to time point t1', conditioning radiation is therefore already supplied to the semiconductor detector element while no x-ray measurement is yet being performed in a measurement sequence. The first measurement sequence follows on immediately in time after the lead time, and the lead time could be for example 10 seconds in order to reach a defined conditioning.

The lead time can be determined or controlled or regulated on the basis of a nominal value or also on a monitoring measured value, just like the control or regulation of the intensity of or the spectrum used for the conditioning radiation during the lead time or also during the measurement sequence. The continuous irradiation is particularly advantageously performed with the aid of the described radiation sources that emit no x-ray radiation.

In addition, variant B also includes the case (not shown) whereby the conditioning radiation is supplied on a 24-hour basis, in other words effectively around the clock. This continuous irradiation is also based on a nominal value, such that a defined conditioning of the semiconductor detector elements can be achieved.

In addition, the temporal control could be realized according to a further variant C such that, as is shown in FIG. 4, the conditioning radiation is deactivated at the moment in which the x-ray irradiation starts. In the time segment between time points t1" and t2", conditioning radiation K is supplied while no x-ray radiation R to be detected is incident on the semiconductor detector element. This is also the case in the time segment between time points t3" and t4". Immediately with the commencement of the x-ray irradiation at time point t2" or t4", however, the supply of the conditioning radiation is stopped, with the result that only x-ray radiation R is detected in the time segments between time points t2" and t3" or t4" and t5", while the supply of the conditioning radiation K is stopped or interrupted. With the aid of this approach it can be ensured that the semiconductor detector element always experiences one type of irradiation and preferably on average over time always the same effect due to the irradiation or illumination.

As has been mentioned repeatedly, the x-ray detector system can be adapted with the aid of the invention to match different x-ray detection requirements, in computed tomography for example.

Figure 5:
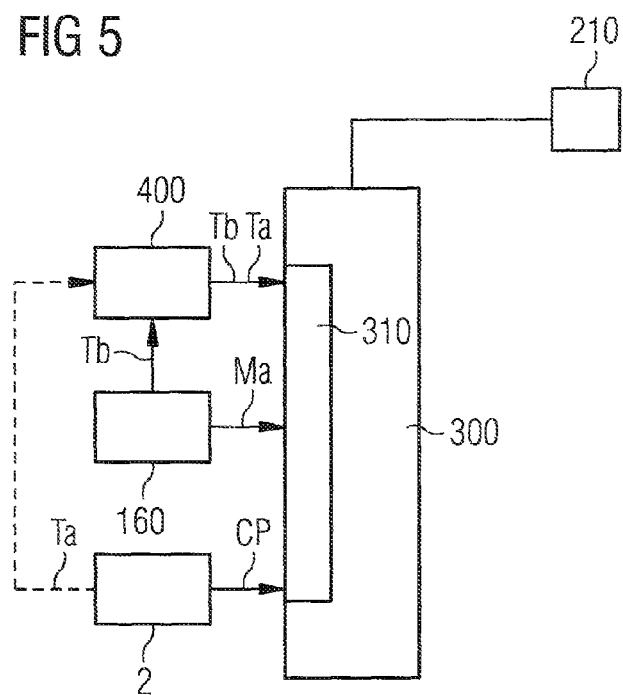
FIG. 5 shows a control unit for controlling the supply of conditioning radiation, having an input interface via which nominal values, monitoring values and other input parameters can be forwarded to the control unit.

FIG. 5 shows an example embodiment of a control unit 300 with the aid of which an adaptation of the detector system to match different imaging or detection requirements can be realized.

As already described, a relatively complex correlation function can be produced which in this example embodiment is forwarded to the control unit 300 with the aid of the input interface 310.

According to at least one embodiment of the invention, the supply of the conditioning radiation is controlled or regulated on the basis of one or more nominal values Ta, Tb, which can be taken into account simultaneously, for example. These can be forwarded e.g. by the mentioned nominal value storage unit 400 to the input interface 310.

Furthermore, monitoring values Ma which are measured with the aid of a monitoring unit 160 can be referred to for controlling or regulating and in particular for forming a correlation function. At the same time the monitoring unit 160 can also be used, as has already been described with reference to FIG. 2, for specifying or measuring a nominal value Tb in order for example to determine the calibration.

In addition, however, further input parameters CP can also be forwarded to the input interface 310 by other measurement systems 2 (such as e.g. temperature sensors, etc.). The parameters can be based for example on parameter values that are available within the detector system, such as e.g. current consumption of the semiconductor detector element or count rate. In particular, the input parameters CP can be formed by way of measured values or derived variables which are based on ambient conditions or also measurement variables or data available within the computed tomography system. For example, the ambient temperature can be determined by way of a thermometer, and the emitted radiation, in particular the x-ray radiation, by way of a dosimeter. However, other operating parameters, such as the total operating time of the detector system or of the computed tomography system or also of the radiation sources, can also form input parameters CP which are taken into account in a complex control and/or regulation of the supply of the conditioning radiation.

Measurement systems such as the monitoring units, for example, or also other measurement systems not associated with the detector system can facilitate for example an active regulation of the irradiation intensity of the semiconductor detector elements. The data of the measurement systems can specify a nominal value Ta, form an input parameter CP, but also forward a measured value equivalent to a monitoring measured value Ma as a regulating variable to the control unit.

It is also possible here to adapt the regulation or control to the planned measurement by way of the computed tomography system. For example, a supply of the conditioning radiation can be controlled or regulated on the basis of the selected x-ray intensities, the x-ray spectrum used, and the attenuations or signal strengths that are to be expected. The nominal value in particular can be determined, measured or specified on the basis of these variables, and it is aimed in particular to achieve a control or regulation of the intensity or spectral variation on the basis of the variables.

In addition, it is also possible to include the history of the past measurements in the regulation or control as well and in this way also compensate for aging effects or hysteresis or memory effects, in particular of the semiconductor detector element, or drift effects present, as described later.

As already described, it is possible to control or regulate the intensity of the conditioning radiation as a function of time, of the administered x-ray dose, of the measured detection current or of another variable, such as e.g. current consumption, run time, temperature, or else also humidity.

The expected attenuations or signal strengths can be derived for example in particular from a quick overview image acquisition, called a topogram. This is illustrated in greater detail in particular in FIG. 6.

FIG. 6 shows a CT system 1 having an x-ray source 10 which is arranged opposite an inventive detector system 200 having a control unit and a radiation source for supplying a conditioning radiation. Located between the x-ray source 10 and the detector system 200 is an examination subject, patient or test subject O in a measurement chamber M around which the x-ray source 10 rotates together with the detector system 200 for the purpose of a normal CT measurement. In a quick overview scan, which is often performed with x-ray source and detector stationary with respect to the angle of rotation, so-called topogram data P is generated initially, on the basis of which an advantageous selection of a measurement program can be made for a planned CT examination. The topogram data P is in this case represented merely schematically in the diagram given on the right in FIG. 6, which shows the intensity I(z) of the x-ray radiation R modulated by the test subject O in the spatial direction z.

In this case, in particular expected attenuation values of the x-ray radiation can be estimated. On the basis thereof, the required detector sensitivity for a planned CT examination can be estimated or planned, in other words specified as nominal values. In the case of a somewhat thinner patient or test subject O having lower attenuation values, a higher count rate is required for example than in the case of a fatter subject, so that in the detector system the control can be realized in such a way that a conditioning of the semiconductor detector elements is performed with respect to a maximum count rate, which is equivalent to a required detector sensitivity. The count rate (and consequently the detector sensitivity) therefore determines the nominal value for the control and/or regulation, so that for example initially, in calibration steps according to FIG. 2, a correlation can be determined between maximum count rate and mA value of the radiation sources. In this case it would preferably be aimed to supply the conditioning radiation at a high conditioning radiation intensity for a thinner person O, since this is typically linked to a high detector sensitivity or high maximum count rate.

With the aid of at least one embodiment of the invention, it is accordingly possible not only to prevent or to compensate for long-term effects in the conditioning of the semiconductor detector elements. Relatively short-term adaptations to match the most diverse requirements placed on the detector system can also be realized.

As indicated, the topogram measurement can also be referred to for selecting a measurement protocol. The information relating to the required detector sensitivity can in this case also be taken into account in the selected measurement protocol or be derived on the basis of the selected measurement protocol or already on the basis of the selection of the measurement protocol. It is therefore likewise possible on the basis of the measurement program to specify a maximum count rate as the nominal value so that the conditioning radiation can be controlled or regulated according to a required count rate. In this case the control and/or regulation can then be effected for example with respect to the intensity or also spectral distribution of the conditioning radiation.

In particular it is advantageous if the detector is conditioned in such a way that a count rate drift is minimized.

Figure 7:
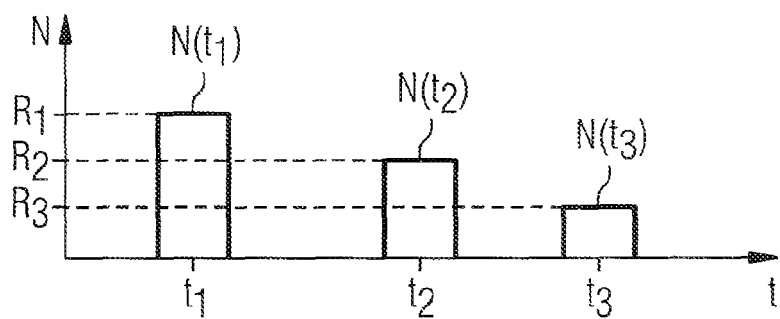
FIG. 7 shows an example of the variation with time of a count rate drift.

FIG. 7 shows an example of a count rate drift. At a constant x-ray dose R1, a count rate N(t1) is determined at a first time point t1. At a later time point t2, given the same administered x-ray dose R1, a count rate N(t2) is determined which corresponds to an x-ray dose R2 that is lower than the actually administered x-ray dose R1. At a third time point t3, a third count rate N(t3) is again determined which corresponds to a third x-ray dose R3 that is in turn lower than the x-ray dose R2 and the actually administered x-ray dose R1. In other words, in this example embodiment of a count rate drift, the count rate decreases while the x-ray dose R1 remains constant. Conversely, it is also possible that at a later time point the count rate will vary toward greater values.

With the aid of the supply of the conditioning radiation it is possible to aim to minimize the count rate drift or to compensate for a count rate drift. To that end e.g. a nominal value can be specified which defines a specific count rate for a specific x-ray dose. The specified nominal value can be determined for example from the history, i.e. from the detection measurements carried out to date, from the operating time of the detector, or on the basis of the conditioning to be expected from the operating characteristics of the detector, or it can be measured directly.

The supply of the conditioning radiation can then be controlled and/or regulated for example on the basis of the specified count rate, for example by increasing or, where necessary, lowering the radiation intensity of the conditioning radiation in order to compensate for the count rate drift. For that purpose, the x-ray dose measured by way of a dosimeter can for example be an input parameter for the control device, with the aid of which a count rate drift, equivalent to a monitoring measured value, can then be estimated and checked.

Figure 8:
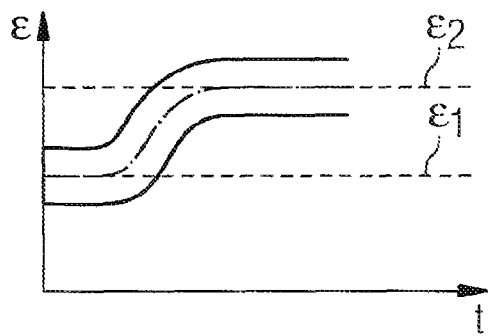
FIG. 8 shows a possibility for determining the nominal value on the basis of the measurement program.

FIG. 8 shows the adjustment or control and/or regulation of the supply of the conditioning radiation on the basis of the energy characteristic curve or the energy selection of the x-ray radiation. Here, the energy $\epsilon$ of the administered x-ray radiation is plotted over time t. In a specific CT acquisition scan that is to be performed, a time characteristic of the energy of the x-ray radiation can be specified, for example. In the illustrated example embodiment, x-ray radiation of a specific spectral width, the mean value of which initially fluctuates around a first energy $\epsilon_1$, is varied into an x-ray energy having identical spectral width, but fluctuating around a higher mean value $\epsilon_2$. This can in turn be taken into account in the required sensitivity of the x-ray detector and in particular in a necessary count rate, so that the supply of the conditioning radiation can be controlled and/or regulated on the basis of the energy characteristic curve of the x-ray source. The energy characteristic curve can for example be specified implicitly by way of a measurement protocol, and the nominal value can then be given by way of a maximum required count rate.

In other words, in particular with regard to the possibilities described with the aid of FIGS. 6 to 8, the control of the supply of the conditioning radiation can be calculated from selected x-ray intensities, the x-ray spectrum used (i.e. the spectral bandwidth of the x-ray radiation) and the expected attenuations or signal strengths. It is also possible to store a specified control or regulation sequence, in particular containing a plurality of target values for specific measurement protocols or measurement sequences of the computed tomography device, in the nominal value storage unit, for example, and to assign the same to the measurement protocol or the measurement sequence. Preferably this is done for each of the x-ray detection measurements that are possible in the device in question.

It should be emphasized in this context that the current irradiation state of the semiconductor detector element can be estimated on the basis of the measurement protocol, and this information can be included in a regulation. In other words, it is possible to estimate exposure levels due to x-ray radiation or operating requirements of the semiconductor detector element in advance if the set measurement parameters (i.e. the measurement protocol) and possibly prior knowledge about the examination subject, based for example on an overview image acquisition (topogram measurement), are factored into the estimation. Accordingly, it is possible for example to eliminate abrupt load changes (i.e. changes occurring e.g. due to sudden displacement of an examination subject relative to the detector) to a large extent and to minimize corresponding effects on the characteristics of the detector system for detection of x-ray radiation accordingly. This can lead to a detector response (or the detection signal associated therewith) that is constant with respect to time and independent of the administered x-ray dose, with the result that, for example, the image quality of a computed tomography measurement can be increased.

As already explained, the regulation and control can be accomplished on the basis of variable nominal values, i.e. nominal values of a specific variable are specified with different values in chronological succession (i.e. as a sequence of target values).

Figure 9:
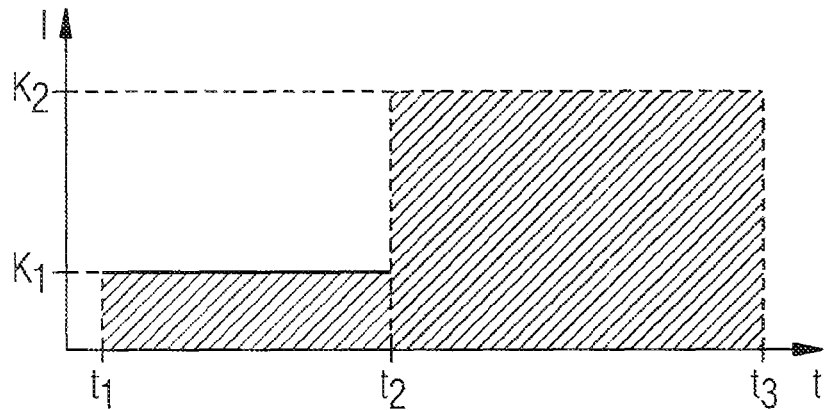
FIG. 9 shows a further time scheme for the emission of conditioning radiation on the basis of variable nominal values.

FIG. 9 shows a corresponding example embodiment. Here, the intensity I of the conditioning radiation is plotted over time t. In the measurement time period between time points t1 and t2, a first nominal value is specified which controls the supply of a first conditioning radiation intensity K1, and in the measurement time period between time points t2 and t3, a target value is specified which controls the supply of a second conditioning radiation intensity K2. It should be emphasized in this context that it is possible for example to vary between different nominal values within a contiguous measurement time period or a contiguous measurement sequence.

It is likewise pointed out in conclusion that the x-ray detector, x-ray detector system and computed tomography system described in detail heretofore are merely example embodiments which can be modified by the person skilled in the art in a multiplicity of different ways without leaving the scope of the invention. It should be pointed out in particular that the features of all of the example embodiments or of developments disclosed in figures may be used in any desired combination. Furthermore, the use of the indefinite articles "a" or "an" does not exclude the possibility that the features in question may also be present more than once. Equally, the term "unit" does not rule out the possibility that the components in question may consist of a number of cooperating subcomponents which, where appropriate, may also be spatially distributed.

The invention claimed is:

1. A method for detecting x-ray radiation by way of an x-ray detector including a direct-conversion semiconductor detector element, comprising:
   supplying a conditioning radiation to the semiconductor detector element for varying polarization effects in the semiconductor detector element with the aid of a conditioning radiation source prior to supplying an imaging radiation to the semiconductor detector with the aid of the radiation source;
   measuring the conditioning radiation at the semiconductor detector element;
   determining a nominal value of the conditioning radiation based on the measured conditioning radiation, the nominal value representing a nominal measured value, including at least one of duration or time point of the supply of the conditioning radiation or x-ray radiation, operating time of the semiconductor detector, radiation intensity of the conditioning radiation or x-ray radiation, radiation density of the conditioning radiation or x-ray radiation, count rate of the conditioning radiation or x-ray radiation, and dose of the conditioning radiation or x-ray radiation; and
   at least one of controlling and regulating the supply of the conditioning radiation from an incident x-ray radiation source based on the determined nominal value, where the conditioning radiation is supplied while no incident radiation to be detected is incident on the semiconductor detector element.

2. The method of claim 1, wherein the radiation source comprises at least one component from the group UV light source, IR light source, light source for visible light, a laser, a halogen lamp, and a tubular fluorescent lamp.

3. The method of claim 1, wherein the radiation source comprises the x-ray source.

4. The method of claim 1, wherein the supply of the conditioning radiation is at least one of controlled and regulated with respect to at least one of time, the radiation density and energy.

5. The method of claim 1, wherein a monitoring measured value corresponding to the nominal value is acquired.

6. The method of claim 1, wherein a monitoring unit for acquiring a monitoring measured value comprises at least one component from the group
   light sensor,
   x-ray sensor,
   semiconductor detector element of the x-ray detector,
   evaluation electronics of the x-ray detector,
   dosimeter,
   thermometer, and
   luxmeter.

7. The method of claim 1, wherein the supply of the conditioning radiation is at least one of controlled and regulated based on the characteristics of an examination subject which is to be transradiated by the x-ray radiation that is to be detected.

8. The method of claim 1, wherein the supply of the conditioning radiation is at least one of controlled and regulated based on at least one of
   the characteristic curve of the emission of the x-ray radiation by way of the x-ray source and
   the attenuation of the x-ray radiation of the x-ray source by the examination subject.

9. The method of claim 1, wherein the supply of the conditioning radiation is at least one of controlled and regulated based on a count rate drift of x-ray quanta.

10. The method of claim 1, wherein the supply of the conditioning radiation is effected on the basis of at least one of the variables
irradiation time,
administered dose,
value or characteristic curve of the detection signal,
total operating time of the detector,
temperature,
humidity,
current consumption of a semiconductor detector element, and
current consumption of a group of semiconductor detector elements.

11. The method of claim 1, wherein the conditioning radiation is supplied in a time window in which the x-ray source emits no x-ray radiation.

12. The method of claim 1, wherein the conditioning radiation is supplied during the entire operating time of the x-ray detector.

13. The method of claim 1, wherein the supply of the conditioning radiation is at least one of controlled and regulated in such a way that at least one of
the intensity and the spectral distribution is determined or monitored, and
the current consumption of at least one of the semiconductor detector elements and a group of semiconductor detector elements is substantially constant.

14. An x-ray detector system, comprising:
an x-ray detector to detect radiation of an x-ray source which includes a direct-conversion semiconductor detector element;
a radiation source to supply a conditioning radiation prior to supplying an imaging radiation to at least one of the semiconductor detector element and a control interface for driving a radiation source; and
a control unit configured to
measure an intensity of the conditioning radiation,
determine a nominal value of the conditioning radiation, and
at least one of control and regulate the supply of an additional radiation on the basis of the determined nominal value.

15. The x-ray detector system of claim 14, further comprising:
a monitoring unit to acquire a monitoring measured value corresponding to the nominal value.

16. The x-ray detector system of claim 15, wherein the monitoring unit is arranged outside of a primary beam path of the x-ray source to the semiconductor detector element.

17. The x-ray detector system of claim 15, wherein the monitoring unit includes at least one shielding device to protect against radiation of the x-ray source.

18. An x-ray detector for the x-ray detector system of claim 14, further comprising a monitoring unit integrated into the x-ray detector.

19. A computed tomography system comprising the x-ray detector system of claim 14.

20. The x-ray detector system of claim 16, wherein the monitoring unit includes at least one shielding device to protect against radiation of the x-ray source.

21. A computed tomography system comprising the x-ray detector system of claim 15.

22. A computed tomography system comprising the x-ray detector system of claim 16.

23. A computed tomography system comprising the x-ray detector system of claim 17.

24. The method of claim 2, wherein the radiation source comprises the x-ray source.

25. The method of claim 2, wherein the supply of the conditioning radiation is at least one of controlled and regulated with respect to at least one of time, the radiation density and energy.

26. The method of claim 2, wherein a monitoring measured value corresponding to the nominal value is acquired.

27. The method of claim 2, wherein a monitoring unit for acquiring a monitoring measured value comprises at least one component from the group
light sensor,
x-ray sensor,
semiconductor detector element of the x-ray detector,
evaluation electronics of the x-ray detector,
dosimeter,
thermometer, and
luxmeter.

28. The method of claim 2, wherein the supply of the conditioning radiation is at least one controlled and regulated based on the characteristics of an examination subject which is to be transradiated by the x-ray radiation that is to be detected.

29. The method of claim 1, wherein the nominal value is derived from a topogram of a patient.

* * * * *